(12) United States Patent
Sobue et al.

(10) Patent No.: US 8,469,545 B2
(45) Date of Patent: Jun. 25, 2013

(54) PERITONEAL DIALYSIS CONNECTION SYSTEM AND METHOD FOR USING ULTRAVIOLET LIGHT EMITTING DIODES

(75) Inventors: Katsuyoshi Sobue, Toyko (JP); Takeshi Nakajima, Tokyo (JP); Atsushi Matsuzaki, Tokyo (JP); Minoru Okuda, Tokyo (JP)

(73) Assignees: Baxter Healthcare Inc., Deerfield, IL (US); Baxter Healthcare S.A., Glattpark (Opfikon) (CH)

( * ) Notice: Subject to any disclaimer, the term of this patent is extended or adjusted under 35 U.S.C. 154(b) by 0 days.

(21) Appl. No.: 13/468,816

(22) Filed: May 10, 2012

(65) Prior Publication Data

US 2012/0220927 A1    Aug. 30, 2012

Related U.S. Application Data

(63) Continuation of application No. 11/773,824, filed on Jul. 5, 2007, now Pat. No. 8,197,087.

(51) Int. Cl.
*F21S 4/00*    (2006.01)
*A61M 1/28*    (2006.01)

(52) U.S. Cl.
USPC ........... 362/249.02; 362/227; 604/29; 422/24

(58) Field of Classification Search
USPC ................... 422/24, 28, 186.3, 292; 362/227, 362/249.02; 604/29
See application file for complete search history.

(56) References Cited

U.S. PATENT DOCUMENTS

| | | | |
|---|---|---|---|
| 1,896,379 A | 2/1933 | Ross | |
| 2,145,196 A | 1/1939 | Biggs | |
| 2,249,473 A | 7/1941 | Jackson | |
| 3,227,877 A | 1/1966 | Dreyfus | |
| 3,391,951 A | 7/1968 | Miller | |
| 3,413,097 A | 11/1968 | Jungner | |
| 3,626,938 A | 12/1971 | Versaci | |
| 3,709,222 A | 1/1973 | Devries | |
| 3,780,736 A | 12/1973 | Chen | |
| 3,814,680 A | 6/1974 | Wood | |
| 3,840,011 A | 10/1974 | Wright | |

(Continued)

FOREIGN PATENT DOCUMENTS

| | | |
|---|---|---|
| DE | 1936245 | 2/1971 |
| DE | 3210148 | 9/1983 |

(Continued)

OTHER PUBLICATIONS

PCT International Search Report for PCT/US2008/068976 dated Nov. 17, 2008.

(Continued)

*Primary Examiner* — Sean E Conley
(74) *Attorney, Agent, or Firm* — K&L Gates LLP

(57) ABSTRACT

Peritoneal dialysis systems are provided by the present disclosure. In a general embodiment, a peritoneal dialysis system includes a cycler, a disposable cassette operable with the cycler, a supply bag connected to the disposable cassette, a supply connector, a supply line extending from the disposable cassette, a patient connector in fluid communication with a patient's indwelling catheter, a device to connect the supply connector to the patient connector, and a housing around the device. The housing includes a plurality of ultraviolet ("UV") light-emitting diodes ("LED's") for directing energy towards at least one of the supply or patient connectors. The LED's are configured to deliver about 200 milliJoules in a period of about a minute.

17 Claims, 2 Drawing Sheets

U.S. PATENT DOCUMENTS

| | | | |
|---|---|---|---|
| 3,916,950 A | 11/1975 | Mongerson et al. |
| 3,926,556 A | 12/1975 | Boucher |
| 3,955,922 A | 5/1976 | Moulthrop |
| 3,957,082 A | 5/1976 | Fuson et al. |
| 3,986,508 A | 10/1976 | Barrington |
| 3,994,686 A | 11/1976 | Rauser et al. |
| 4,056,116 A | 11/1977 | Carter et al. |
| 4,063,890 A | 12/1977 | Baron |
| 4,069,153 A | 1/1978 | Gunther |
| 4,080,965 A | 3/1978 | Phillips |
| 4,096,859 A | 6/1978 | Agarwal et al. |
| 4,121,107 A | 10/1978 | Bachmann |
| 4,141,686 A | 2/1979 | Lewis |
| 4,169,474 A | 10/1979 | Wagner |
| 4,173,234 A | 11/1979 | Thomas |
| 4,196,730 A | 4/1980 | Wilson |
| 4,201,917 A | 5/1980 | Graentzel |
| 4,219,055 A | 8/1980 | Wright |
| 4,219,221 A | 8/1980 | Webb |
| 4,239,041 A | 12/1980 | Popovich et al. |
| 4,242,310 A | 12/1980 | Greff et al. |
| 4,291,701 A | 9/1981 | Bowman |
| 4,306,976 A | 12/1981 | Bazzato |
| 4,338,933 A | 7/1982 | Bayard et al. |
| 4,346,703 A | 8/1982 | Dennehey et al. |
| 4,387,879 A | 6/1983 | Tauschinski |
| 4,405,315 A | 9/1983 | Handt |
| 4,412,834 A | 11/1983 | Kulin et al. |
| 4,433,244 A | 2/1984 | Hogan |
| 4,439,193 A | 3/1984 | Larkin |
| 4,475,900 A | 10/1984 | Popovich et al. |
| 4,500,788 A | 2/1985 | Kulin et al. |
| 4,503,333 A | 3/1985 | Kulin et al. |
| 4,541,829 A | 9/1985 | Munsch et al. |
| 4,557,727 A | 12/1985 | Handt |
| 4,596,551 A | 6/1986 | Golinski et al. |
| 4,617,012 A | 10/1986 | Vaillancourt |
| 4,626,245 A | 12/1986 | Weinstein |
| 4,626,845 A | 12/1986 | Ley |
| 4,655,753 A | 4/1987 | Bellotti et al. |
| 4,655,762 A | 4/1987 | Rogers |
| 4,675,007 A | 6/1987 | Terry |
| 4,695,276 A | 9/1987 | Shinno et al. |
| 4,738,668 A | 4/1988 | Bellotti et al. |
| 4,755,292 A | 7/1988 | Merriam |
| 4,769,017 A | 9/1988 | Fath et al. |
| 4,774,415 A | 9/1988 | Biegel et al. |
| 4,840,621 A | 6/1989 | Larkin et al. |
| 4,869,286 A | 9/1989 | Williams et al. |
| 4,873,446 A | 10/1989 | Kreitmair et al. |
| 4,878,516 A | 11/1989 | Mathieu |
| 4,882,496 A | 11/1989 | Bellotti et al. |
| 4,952,812 A | 8/1990 | Miripol et al. |
| D310,881 S | 9/1990 | Larkin et al. |
| 5,014,494 A | 5/1991 | George |
| 5,047,011 A | 9/1991 | Caron et al. |
| 5,057,074 A | 10/1991 | Suzuki et al. |
| 5,125,911 A | 6/1992 | Grabenkort et al. |
| 5,184,020 A | 2/1993 | Hearst et al. |
| 5,250,041 A | 10/1993 | Folden et al. |
| 5,279,605 A | 1/1994 | Karrasch et al. |
| 5,311,899 A | 5/1994 | Isayama et al. |
| 5,334,139 A | 8/1994 | Jeppsson et al. |
| 5,399,156 A | 3/1995 | Lindsay |
| 5,472,720 A | 12/1995 | Rakhimov et al. |
| 5,540,265 A | 7/1996 | Polaschegg et al. |
| 5,542,913 A | 8/1996 | Lindsay |
| 5,572,992 A | 11/1996 | Kankkunen et al. |
| 5,583,948 A | 12/1996 | Shibayama |
| 5,612,001 A | 3/1997 | Matschke |
| 5,647,984 A | 7/1997 | Hovland et al. |
| 5,707,911 A | 1/1998 | Rakhimov et al. |
| 5,714,119 A | 2/1998 | Kawagoe et al. |
| 5,733,457 A | 3/1998 | Hovland et al. |
| 5,792,419 A | 8/1998 | Williamson et al. |
| 5,843,379 A | 12/1998 | Kristensen |
| 5,900,211 A | 5/1999 | Dunn et al. |
| 5,925,014 A | 7/1999 | Teeple, Jr. |
| 5,948,247 A | 9/1999 | Gillerfalk et al. |
| 6,013,918 A | 1/2000 | Bushnell et al. |
| 6,146,600 A | 11/2000 | Williamson |
| 6,171,561 B1 | 1/2001 | Williamson et al. |
| 6,228,332 B1 | 5/2001 | Dunn et al. |
| 6,234,538 B1 | 5/2001 | Lauer |
| 6,245,570 B1 | 6/2001 | Grimm et al. |
| 6,293,921 B1 | 9/2001 | Shinmoto et al. |
| 6,440,095 B1 | 8/2002 | Utterberg |
| 6,443,147 B1 | 9/2002 | Matter |
| 6,461,568 B1 | 10/2002 | Eckhardt |
| 6,468,424 B1 | 10/2002 | Donig et al. |
| 6,565,525 B1 | 5/2003 | Burbank et al. |
| 6,565,803 B1 | 5/2003 | Bolton et al. |
| 6,696,023 B2 | 2/2004 | Grimm et al. |
| 6,730,113 B2 | 5/2004 | Eckhardt et al. |
| 6,736,797 B1 | 5/2004 | Larsen et al. |
| 6,814,726 B1 | 11/2004 | Lauer |
| 6,911,025 B2 | 6/2005 | Miyahara |
| 7,083,605 B2 | 8/2006 | Miyahara |
| 7,195,615 B2 | 3/2007 | Tan |
| 7,232,429 B2 | 6/2007 | Moreci |
| 7,306,197 B2 | 12/2007 | Parrino et al. |
| 2003/0017073 A1 | 1/2003 | Eckhardt et al. |

FOREIGN PATENT DOCUMENTS

| | | |
|---|---|---|
| EP | 0311848 | 4/1989 |
| EP | 0482858 | 4/1989 |
| EP | 0575970 | 12/1993 |
| EP | 0687474 | 12/1995 |
| JP | 2008-068049 | 3/2008 |
| JP | 2008068049 | 3/2008 |
| WO | 86/04674 | 8/1986 |
| WO | 92/11046 | 7/1992 |
| WO | 96/25214 | 8/1996 |
| WO | 2008/014437 | 1/2008 |

OTHER PUBLICATIONS

EP Office Action for Application No. 08 772 340.9-2320 dated Dec. 11, 2012.

Japanese Office Action mailed Jan. 10, 2013, corresponding to Japanese Application No. 2010-515248.

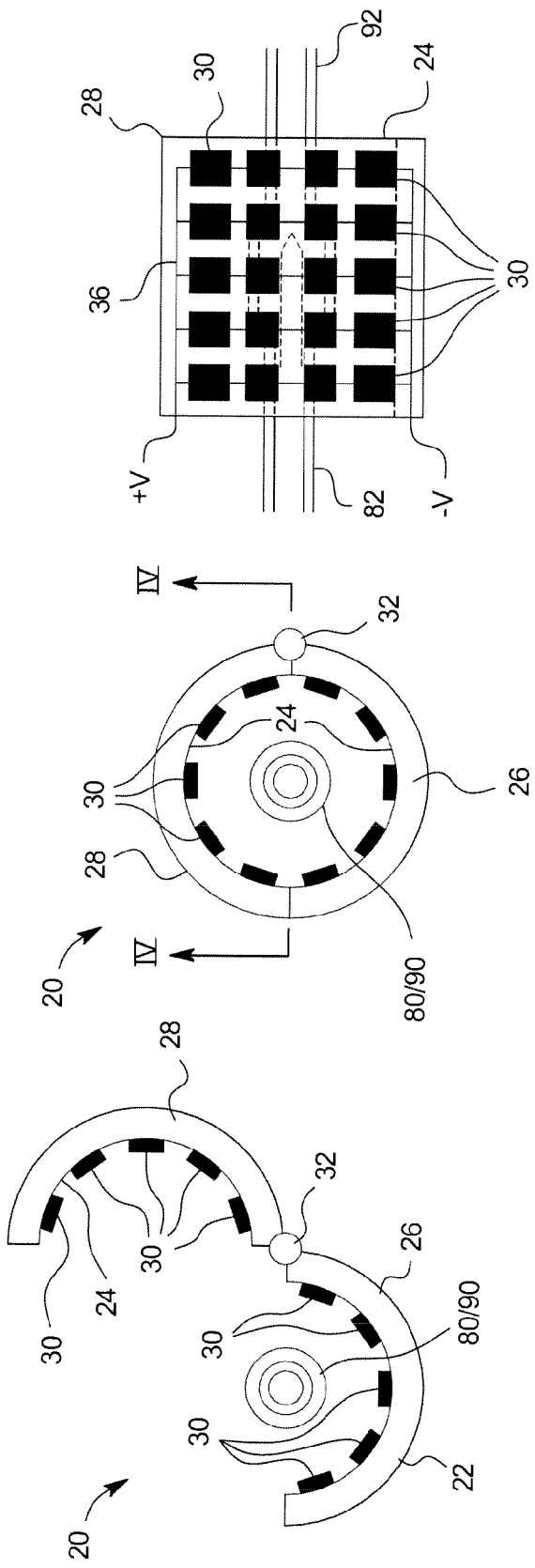

PERITONEAL DIALYSIS CONNECTION SYSTEM AND METHOD FOR USING ULTRAVIOLET LIGHT EMITTING DIODES

PRIORITY CLAIM

This application claims priority to and the benefit as a continuation application of U.S. patent application Ser. No. 11/773,824, filed Jul. 5, 2007, entitled, "Peritoneal Dialysis Patient Connection System Using Ultraviolet Light Emitting Diodes," the entire contents of which are incorporated herein by reference and relied upon.

BACKGROUND

The present disclosure relates generally to medical device connectors and more specifically to sterilized patient connection systems for peritoneal dialysis.

Due to various causes, a person's renal system can fail. Renal failure produces several physiological derangements. The balance of water, minerals and the excretion of daily metabolic load is no longer possible and toxic end products of nitrogen metabolism (urea, creatinine, uric acid, and others) can accumulate in blood and tissue.

Kidney failure and reduced kidney function have been treated with dialysis. Dialysis removes waste, toxins and excess water from the body that would otherwise have been removed by normal functioning kidneys. Dialysis treatment for replacement of kidney functions is critical to many people because the treatment is life saving.

One type of kidney failure therapy is peritoneal dialysis, which uses a dialysis solution, also called dialysate, which is infused into a patient's peritoneal cavity via a catheter. The dialysate contacts the peritoneal membrane of the peritoneal cavity. Waste, toxins and excess water pass from the patient's bloodstream, through the peritoneal membrane and into the dialysate due to diffusion and osmosis, i.e., an osmotic gradient occurs across the membrane. The spent dialysate is drained from the patient, removing waste, toxins and excess water from the patient. This cycle is repeated.

There are various types of peritoneal dialysis therapies, including continuous ambulatory peritoneal dialysis ("CAPD"), automated peritoneal dialysis ("APD"), tidal flow dialysate and continuous flow peritoneal dialysis ("CFPD").

The technique of CAPD to remove impurities from the blood of a patient whose kidneys have failed permits the patient being dialyzed to carry a surgically implanted catheter, which is generally connected (intermittently) to a peritoneal dialysis transfer set. For CAPD treatment, the transfer set, in turn, is connected to a bag of peritoneal dialysis solution, which is emptied through the transfer set into the peritoneal cavity (CAPD infusion phase). For CAPD, the patient is not "tied" to a machine and can be ambulatory while the dialysis across the peritoneal membrane (CAPD dwell phase) occurs. After the dwell phase, the peritoneal dialysis solution is drained (CAPD drain phase) from the peritoneal cavity. This can be done by allowing the solution to flow back into the supply bag; there is preferably no disconnection of the bag during the dwell phase. After the drain phase, the bag with spent peritoneal dialysis solution may be disconnected from the transfer set and discarded.

Automated peritoneal dialysis ("APD") is similar to CAPD in that the dialysis treatment includes drain, fill, and dwell cycles. APD machines or "cyclers", however, perform the cycles automatically, typically while the patient sleeps. APD machines free patients from having to manually perform the treatment cycles and from having to transport supplies during the day. APD machines connect fluidly to an implanted catheter, to a source or bag of fresh dialysate and to a fluid drain. APD machines pump fresh dialysate from a dialysate source, through the catheter, into the patient's peritoneal cavity, and allow the dialysate to dwell within the cavity, and allow the transfer of waste, toxins and excess water to take place. The source can be multiple sterile dialysate solution bags.

APD machines pump spent dialysate from the peritoneal cavity, though the catheter, to the drain. As with the manual process, several drain, fill and dwell cycles occur during dialysate. A "last fill" occurs at the end of CAPD and APD, which remains in the peritoneal cavity of the patient until the next treatment.

Both CAPD and APD are batch type systems that send spent dialysis fluid to a drain. Tidal flow systems are modified batch systems. With tidal flow, instead of removing all of the fluid from the patient over a longer period of time, a portion of the fluid is removed and replaced after smaller increments of time.

Continuous flow, or CFPD, systems clean or regenerate spent dialysate instead of discarding it. The systems pump fluid into and out of the patient, through a loop. Dialysate flows into the peritoneal cavity through one catheter lumen and out another catheter lumen. The fluid exiting the patient passes through a reconstitution device that removes waste from the dialysate, e.g., via a urea removal column that employs urease to enzymatically convert urea into ammonia. The ammonia is then removed from the dialysate by adsorption prior to reintroduction of the dialysate into the peritoneal cavity. Additional sensors are employed to monitor the removal of ammonia. CFPD systems are typically more complicated than batch systems.

All of the above systems require the patient to connect the patient's indwelling catheter to a PD supply apparatus via a transfer set. The patient connection must be kept sterile or the patient can suffer from a condition called peritonitis. The patient connection should also be easy for the patient to make and unmake because the patient is usually performing these tasks at home and/or alone. Accordingly, a need exists for improved peritoneal dialysis patient connection systems.

SUMMARY

The present disclosure includes a system and method for connecting supply connectors to a patient for medical systems making such connections. Such connections need to be made in a sterilized environment in many cases so that contaminants from the supply connectors or from the connection process do not reach the patient. In peritoneal dialysis for example, a catheter is implanted into the patient's peritoneal cavity. The catheter terminates outside the body with a port. The port is connected to what is termed a patient transfer set. The patient transfer set, in turn, is connected to a supply line, extending for example from a supply bag (typical with manual peritoneal dialysis ("CAPD")) or from a disposable cassette.

The present disclosure provides a light-emitting applicator that surrounds the above-described connection, so that it can be made in a sterilizing environment. The applicator includes a housing, which is hinged to permit placement of a connection mechanism holding the connectors within the light applicator. The inner surface of the housing can have an ultraviolet ("UV") light-reflecting material, for example, an etched aluminum coating, to maximize the exposure of ultraviolet light applied to the contents of within the applicator. The connection mechanism is light-transmissive to allow light from the applicator to reach the connectors held by the connection mechanism.

Traditional UV light elements have used Xenon lamps. The Xenon lamps however require a relatively high operating voltage, e.g., on the order of hundreds of volts, to generate enough light energy. In the present disclosure, the light applicator includes a series of ultraviolet light emitting diodes ("LED's") that replace the Xenon lamp. The UV-LED's do not require the same high voltage, allowing the light applicator to be made lighter and smaller.

The UV-LED's are spaced in an array about an inner surface of the light applicator, which can be at least substantially cylindrical. As mentioned, the cylindrical housing of the light applicator is hinged in one embodiment to allow a patient assist connection device to be loaded into the applicator. The light applicator also includes circuitry that connects to a power source, the circuitry operable to apply power to each of the UV-LED's simultaneously, so that the UV-LED's collectively supply a proper amount of power over a period of time to effectively disinfect the connectors of the patient set being connected or disconnected. The power source can be a battery source allowing for cordless operation, or an AC source, such as from a wall unit or from the PD cycler.

In an alternative embodiment, the power source is shifted to power the UV-LED's sequentially, e.g., full power to half of the UV-LED's for a period of time, then full power to the other half of the UV-LED's for the time period, and so on over the full period of irradiation. Power can be divided into sequential thirds or quarters and is not limited to being divided into halves. Further alternatively, the power source is manipulated to switch back and forth between simultaneous and sequential powering over the total time as many times as desired.

In one implementation each UV-LED radiates one milli-Watt of UV energy at a peak wavelength of 280 nanometers. If 0.2 Joules/cm$^2$ of total energy per unit area is needed, fifty UV-LED's can be placed in an array on the inner surface of the housing of the light applicator to provide the needed total energy over a workable time as described in more detail below. The UV-LED's are capable of irradiating the transversely disposed interior surfaces of the system, for example, the outer surface of a diaphragm initially covering a female (e.g., supply) connector, prior to its rupturing. The UV-LED's also irradiate the complex surfaces of the spike of the spike connector.

The light applicator in one embodiment includes a photocell that measures the total energy of ultraviolet light applied in each sterilization procedure. When the total energy reaches a predetermined overall desired exposure level, for example, about two-hundred milliJoules per unit area ("mJ")/cm$^2$, the photocell activates a transducer connected to the photocell to shut off the ultraviolet light element. The overall exposure time depends on the microbiological load to be disinfected. Alternatively, the amount of energy required to produce an appropriate germicidal level is determined by microbiological evaluation before connection, yielding a total time of exposure needed. The light applicator is then energized for the predetermined time of exposure. Either way, the energy exposure level assures maximum antimicrobial effect on the spike and female connector.

BRIEF DESCRIPTION OF THE FIGURES

FIG. 2 is an end view of the ultraviolet ("UV") light-emitting diode ("LED") applicator of the system of FIG. 1, showing the connectors for reference, and illustrating that the applicator in one embodiment is hinged.

FIG. 3 is the end view of FIG. 2 showing the applicator closed about the connectors, such that the UV-LED's of the applicator are positioned to emit light onto the connectors from many different angles.

FIG. 4 is a side elevation view of a section taken along line IV-IV of FIG. 3.

DETAILED DESCRIPTION

Figure 1:
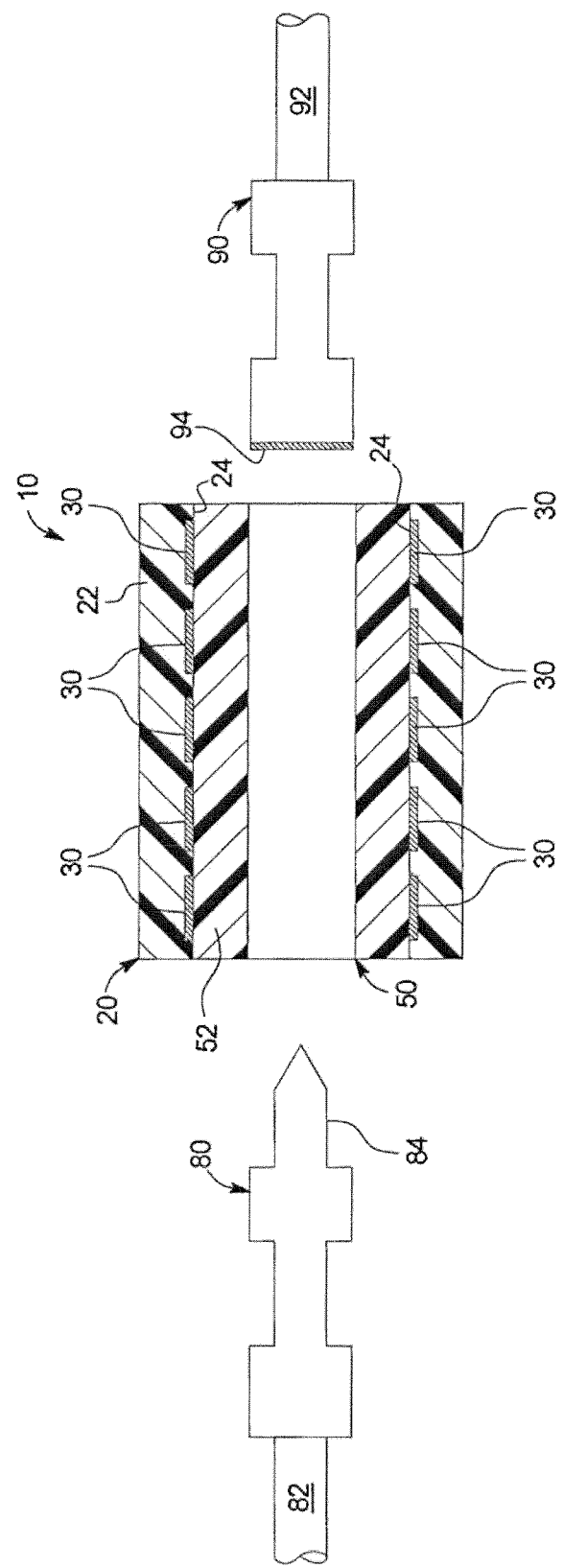
FIG. 1 illustrates an embodiment of a patient assist system of the present disclosure.

The apparatus and method discussed herein are illustrated in use with a peritoneal dialysis system, such as continuous ambulatory peritoneal dialysis ("CAPD") or an automated peritoneal dialysis ("APD"). It should be appreciated however that the teachings associated with the appended drawings are applicable to many types of medical fluid systems. In CAPD and APD, the patient connects a supply line running to either a supply bag directly (CAPD) or to a disposable cassette (APD) operable with a pumping cycler. It is important that such connection be made in a sterile manner. It is also desirable to have a convenient system for the patient, who may be ill or elderly, to operate.

The patient connects the supply line to a patient line, which can be part of a PD transfer set, which is in turn connected to a catheter dwelling within the patient's peritoneum. The patient then has to connect the patient line to a drain bag to enable spent dialysate to be removed from the patient's peritoneum. The patient may have to connect multiple supply lines, each running from a separate supply bag, to the patient line. Between each supply bag, the patient has to connect to a drain bag. Here, it is important that the patient be able to disconnect an old supply line, connect a drain line and then connect a new supply line readily and in a sterilizing environment.

Referring now to the drawings and in particular to FIG. 1, system 10 illustrates one embodiment of a patient assist system of the present disclosure. FIG. 1 shows system 10 schematically and generally, highlighting the general physical and operable relationship between the components. System 10 includes an ultraviolet ("UV") light applicator 20. Light applicator 20 includes a housing 22, which can be formed of a plastic or other suitable medical grade material. As shown in more detail below, housing 22 in one embodiment is hinged so that it can fit around a connection/disconnection device 50. A plurality of ultraviolet ("UV") light emitting-diodes ("LED's") 30 are placed on an inner surface 24 of housing 22 of light applicator 20. UV-LED's 30 are positioned to direct energy inwardly through a body 52 of connection/disconnection device 50 so as to direct disinfecting light onto a connection and disconnection of a patient connector 80 to and from, respectively, a supply or port connector 90. Body 52 of connection/disconnection device 50 is accordingly made of a UV transmissive material.

Disconnection/reconnection device 50 can have different configurations and still operate within system 10 with UV-LED applicator 20. One suitable disconnection/reconnection device however is disclosed in copending U.S. patent application Ser. No. 11/773,623 ("The '623 application"), filed Jul. 5, 2007, entitled "Peritoneal Dialysis Patient Connection System", assigned to the eventual assignee of the present application, the entire contents of which are incorporated herein by reference.

Patient connector 80 is connected sealingly to a patient tube 82, which can be part of the patient's transfer set and connect fluidly to the patient's indwelling catheter. Supply or port connector 90 in turn is connected to a supply line 92, which can run to either a supply bag directly or to a disposable cassette as described above. Port connector 90 includes a pierceable diaphragm 94. Patient or spike connector 80 includes or defines a spike 84, which pierces or ruptures diaphragm 94 of port connector 90 when the connectors are mated. While patient connector 80 is shown being male in nature and port connector 90 is shown being female in nature, the reverse can alternatively be true. Connectors 80 and 90 are at least partially opaque to UV light in one embodiment.

Connection/disconnection device 50 enables connectors 80 and 90 to be connected and disconnected without physically touching such connectors and potentially contaminating same. Disinfecting light from UV LED's 30 is radiated onto connectors 80 and 90 generally just before the connectors are mated and just after the connectors are disconnected as shown and described in detail in the application.

Referring now to FIGS. 2 to 4, UV applicator 20 is illustrated in more detail. FIG. 2 shows that housing 22 of UV applicator 20 is at least substantially cylindrical in shape in one embodiment and includes halves 26 and 28, separated by a hinge 32. Hinge 32 allows halves 26 and 28 to be fitted about connection/disconnect device 50, which holds connectors 80 and 90 shown for reference in FIGS. 2 and 3.

FIG. 3 shows halves 26 and 28 closed about connectors 80 and 90. UV-LED's 30 are positioned to radiate energy onto the connection or disconnection of connectors 80 and 90. The at least substantially cylindrical shape of housing 22 focuses the light from each of UV-LED's 30 towards a centerline running through applicator 20, and thus towards the connectors. FIG. 4 is a view of the inner surface 24 of half 28 of housing 22 of light applicator 20, taken along line IV-IV shown in FIG. 3

FIG. 4 shows that each half 26 and 28 includes a five-by-five array of UV-LED's 30. Trace wires 36 are formed on inner surface 24 of halves 26 and 28 in one embodiment to power each UV-LED 30 simultaneously, so that the UV-LED's 30 supply a collective amount of energy to disinfect the connection and disconnection of connectors 80 and 90. As seen in FIG. 4, trace wires 34 terminate at power supply terminals V+ and V−. In an embodiment, a single pair of power supply terminals V+ and V− is provided for the UV-LED's 30 of both halves 26 and 28. UV-LED's 30 can be powered from a direct current ("DC") source, such as an onboard replaceable or rechargeable battery, or by an alternating current source, for example, via a wall outlet or from a cycler or base instrument.

In an alternative embodiment, software and circuitry are configured to shift the power source to power the UV-LED's 30 sequentially, e.g., full power to half 26 of the UV-LED's 30 for a period of time, then full power to the other half 28 of the UV-LED's 30 for the time period, and so on over the full period of irradiation. Full power can alternatively be shifted sequentially between halves, thirds, quarters or otherwise as desired. Further alternatively, the software and circuitry is configured to manipulate the power source to switch back and forth between simultaneous and sequential powering of UV-LED's 30 over the total time as many times as desired.

In an embodiment, each LED 30 operates on 0.6 Volts at 20 mA, leading to a power requirement of 120 milliWatt/per LED 30. Fifty total LED's 30 would then require an overall power requirement of six Watts. This is significantly less than the approximately forty-three Watts required by the Xenon lamp applicator.

Inner surfaces 24 of halves 26 and 28 in one embodiment include a UV light reflective material, for example, an etched aluminum coating, which maximizes the exposure of UV light that UV-LED's 30 impart onto connectors 80 and 90. The material of housing 22 is otherwise made of a suitable medical grade material, which is relatively inexpensive, such as plastic, e.g., methacrylic resin yellow.

One suitable UV-LED 30 is provided from Seoul Semiconductor Co., Ltd, 148-29 Gasan-dong Geumcheon-gu Seoul, Korea, model number S8D28D. In one embodiment, each UV-LED 30 has a peak wavelength of about 280 nanometers. Each UV-LED 30 has a power output of about one milliWatt. If a predetermined proper disinfection of connectors 80 and 90 requires about 0.2 Joules in total energy, for example, fifty UV-LED's 30 are sufficient at the above rating to supply the needed energy over a suitable time period.

The five-by-five array of UV-LED's 30 in FIG. 4 is repeated on hinged half 26 to provide the fifty total UV-LED's 30. In one embodiment, the fifty UV-LED's 30 are spread out evenly over halves 26 and 28 of housing 22, which in one implementation has a ten mm inner diameter and forty mm length, e.g., roughly the size of the spike 84 of connector 80. Housing 22 can alternatively be larger, e.g., be large enough to encompass the connection/disconnection device of the '623 application. The '623 application discloses a hinged system in which half of the connection/disconnection device is connected to a lid, which is hinged to a housing holding motors and other apparatuses for automatic connection and disconnection of the connectors. In use with the connection/disconnection device of the '623 application, halves 26 and 28 would likely not be hinged to each other but instead place in the above-mentioned lid and housing, which are in turn hinged to each other. Applicator 20 accordingly does not have to be hinged to itself Each separate half could have its own power supply V+ and V−, which could be powered simultaneously to provide the needed total power. It should also be appreciated that in any configuration (hinged or separate), inner surfaces 24 of halves 26 and 28 can be removed for cleaning.

The combined radiation from fifty UV-LED's 30 provides a light intensity or luminance ($L^{ux}$) equal to (1 milliWatt×50 UV-LED's)/(10 mm×π×40 mm)=4 millWatts/cm².

The UV effectiveness energy $L^{ux}$eff, knowing that the Xenon wavelength is 254 nanometers ("nm") and that a 280 nm LED has a 90% sterilization efficiency to 254 nm light (Xenon or LED), then $L^{ux}$eff=4 milliWatts/cm²×0.9=3.6 milliWatts/cm². Given a UV effectiveness for the fifty UV-LEDs of 3.6 milliJoules, the time required for a total energy output per unit area of 0.2 Joules/cm² is as follows: time of radiation=200 milliJoules/cm²/3.6 milliWatts/cm²=56 seconds.

Another way of evaluating time of exposure, Xenon wavelength of 254 nm is used as a benchmark. That is, 200 mJ/cm² of Xenon light is sufficient for proper disinfection. It is therefore taken that 200 mJ/cm² of 254 nm UV-LED light is also sufficient sterilization. Sterilization efficiency of 280 nm UV-LED is 0.9×254 nm, whether UV-LED or Xenon light is used. So if 280 nm UV-LED light is used, 200 mJ/cm²/0.9=222 mJ/cm² needs to be applied to the connector, e.g., spike connector 80. The spike 84 of connector 80 as discussed can be ten mm×four mm, yielding surface area S=10 mm×π×40 mm=(4×π) cm². Fifty 280 nm LED's yield an output of 50 mW=50 mJ/second. Applicator 20 can accordingly deliver 50 mW/S=50/(4×π) mJ/cm²/second. Knowing that 222 mJ is needed, fifty 280 UV-LED's will illuminate 222×(4×π)/50 in 55.8 seconds.

Fifty-six seconds of irradiation is an acceptable amount of time for the patient when connecting or disconnecting connectors 80 and 90. The relatively small size of UV-LED's 30 and their associated relatively small power requirement The invention is claimed as follows:

1. A peritoneal dialysis system comprising:
a cycler;
a disposable cassette operable with the cycler;
a supply bag connected to the disposable cassette;
a supply connector;
a supply line extending from the disposable cassette, the supply line terminating at the supply connector;
a patient connector in fluid communication with a patient's indwelling catheter;
a device configured to connect the supply connector to the patient connector without physically contacting the supply connector and the patient connector; and
a housing placeable around the device and including a plurality of ultraviolet ("UV") light-emitting diodes ("LED's") positioned to direct energy towards at least one of the supply connector and the patient connector, wherein the plurality of LED's are configured to deliver about 200 milliJoules in a period of about a minute.

2. The peritoneal dialysis system of claim 1, wherein at least one of the supply connector and the patient connector is at least partially opaque to UV light.

3. The peritoneal dialysis system of claim 1, wherein the at least one UV-LED is powered via a battery.

4. The peritoneal dialysis system of claim 1, wherein the at least one UV-LED is powered via the cycler.

5. The peritoneal dialysis system of claim 1, which includes a transfer set, the transfer set connecting the patient connector to the indwelling catheter.

6. The peritoneal dialysis system of claim 1, wherein the housing is hinged or halved to fit around the connecting device.

7. The peritoneal dialysis system of claim 1, which is configured to emit UV light from the LED's just before the supply connector and the patient connector are mated via the device.

8. The peritoneal dialysis system of claim 1, which is configured to emit UV light from the LED's just after the supply connector and the patient connector are disconnected via the device.

9. A peritoneal dialysis system comprising:
a cycler;
a disposable cassette operable with the cycler;
a supply bag;
a supply connector;
a supply line positioned and arranged to carry dialysis fluid from the supply bag to the supply connector;
a patient connector in fluid communication with a patients' indwelling catheter; and
a housing placeable around the supply connector and the patient connector, the housing including a plurality of ultraviolet ("UV") light-emitting diodes ("LED's") positioned to direct energy towards all mating surfaces of both of the supply connector and the patient connector (i) just prior to connecting the supply connector and the patient connector and/or (ii) just after disconnecting the supply connector and the patient connector.

10. The peritoneal dialysis system of claim 9, which includes a cycler and a disposable cassette operable with the cycler, at least one of the supply bag and the supply line in fluid communication with the disposable cassette.

11. The peritoneal dialysis system of claim 9, which includes a device configured to connect and disconnect the supply connector and the patient connector, and wherein the housing is placeable around the device.

12. The peritoneal dialysis system of claim 9, wherein an inner surface of the housing includes a UV light reflective material.

13. The peritoneal dialysis system of claim 9, wherein the plurality of LED's are connected together electrically via at least one trace wire formed on an inner surface of the housing.

14. The peritoneal dialysis system of claim 9, wherein each of the LED's has a power output of about 4 milliJoule per second at an output wavelength of about 280 nanometers.

15. The peritoneal dialysis system of claim 9, wherein the plurality of LED's includes about fifty mounted LED's and the housing includes two cylindrical halves.

16. The peritoneal dialysis system of claim 9, wherein the plurality of LED's includes about fifty LED's and the housing includes two cylindrical halves, each half being about ten mm inner diameter and about 40 mm long.

17. The peritoneal dialysis system of claim 9, which is configured to power a first portion of the plurality of LED's for a period of time and a second portion of the plurality of LED's after the period of time.

* * * * *